US008632819B2

United States Patent
Thoorens et al.

(10) Patent No.: US 8,632,819 B2
(45) Date of Patent: Jan. 21, 2014

(54) MICROCRYSTALLINE CELLULOSE AND CALCIUM CARBONATE COMPOSITIONS USEFUL AS RECOMPACTIBLE PHARMACEUTICAL EXCIPIENTS

(75) Inventors: Gregory Thoorens, Ganshoren (BE); Bruno LeClercq, Brussels (BE); Thomas Ruszkay, Hockessin, DE (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 12/962,992

(22) Filed: Dec. 8, 2010

(65) Prior Publication Data

US 2011/0151014 A1    Jun. 23, 2011

Related U.S. Application Data

(60) Provisional application No. 61/289,061, filed on Dec. 22, 2009.

(51) Int. Cl.
*A61K 9/16* (2006.01)
*A61K 9/20* (2006.01)
*A61K 47/38* (2006.01)
*G01N 3/08* (2006.01)

(52) U.S. Cl.
USPC ........... 424/499; 424/400; 424/465; 424/602; 241/27

(58) Field of Classification Search
None
See application file for complete search history.

(56) References Cited

U.S. PATENT DOCUMENTS

| | | | | |
|---|---|---|---|---|
| 4,744,987 | A | * | 5/1988 | Mehra et al. ................ 424/687 |
| 5,356,896 | A | * | 10/1994 | Kabadi et al. ................ 514/256 |
| 5,747,067 | A | | 5/1998 | Auguello et al. |
| 6,037,380 | A | | 3/2000 | Venables et al. |
| 6,936,277 | B2 | | 8/2005 | Staniforth et al. |
| 6,936,628 | B2 | | 8/2005 | Lee |
| 2005/0244521 | A1 | * | 11/2005 | Strickland et al. ........... 424/751 |
| 2007/0172524 | A1 | | 7/2007 | Klobcar et al. |
| 2008/0213360 | A1 | | 9/2008 | Thoorens et al. |

FOREIGN PATENT DOCUMENTS

| | | |
|---|---|---|
| WO | WO 81/02521 A1 | 9/1981 |
| WO | WO 03/096963 A1 | 11/2003 |
| WO | WO 2005/030115 A1 | 4/2005 |
| WO | WO 2005/030116 A1 | 4/2005 |
| WO | WO 2005/030379 A1 | 4/2005 |
| WO | WO 2006/032828 A1 | 3/2006 |

OTHER PUBLICATIONS

Product information for Avicel 102 downloaded from the internet on Apr. 4, 2012 from the site: http://www.fmcbiopolymer.com/Pharmaceutical/Products/Avicelforsoliddoseforms.aspx.*
Mesh to micron conversion table downloaded from the internet on Apr. 4, 2012 from the site: http://www.showmegold.org/news/Mesh.htm.*
Maria de Lourdes Garzón Serra and Leopoldo Villafuerte Robles. Compactibility of agglomerated mixtures of calcium carbonate and microcrystalline cellulose. International Journal of Pharmaceutics 258 (2003) 153-163.*
Falzone, Angela Marie—(Thesis) Univ. Of Michigan, Ann Arbor, "Roller Compaction of Pharmaceutical Excipients and Excipient-Drug Blends", 1990. 250 pages.
Fitzpatrick Company Europe "Introduction to Roll Compaction and the Fitzpatrick Chilsonator", Mar. 1997, 18 pages.
Kleinebudde, Peter, "Roll Compaction/Dry Granulation: Pharmaceutical Applications", Institute of Pharmaceutics, Duesseldorf, Germany. European Journal of Pharmaceutics and Biopharmaceutics 58, pp. 317-326, Apr. 2004.
Notification of Transmittal of The International Search Report and The Written Opinion of the International Searching Authority, or the Declaration, International Filing Date—Dec. 8, 2010, Date of Mailing Aug. 30, 2011.

* cited by examiner

*Primary Examiner* — Frederick Krass
*Assistant Examiner* — Michael P Cohen
(74) *Attorney, Agent, or Firm* — FMC Corporation

(57) ABSTRACT

Coprocessed compositions containing microcrystalline cellulose and calcium carbonate, wherein the weight ratio of microcrystalline cellulose to calcium carbonate is relatively high, are useful as excipients in the preparation of solid dosage forms containing active pharmaceutical ingredients, particularly those prepared by processes involving multiple compaction steps. Such compositions may be obtained, for example, by preparing aqueous slurries or wet masses of microcrystalline cellulose and calcium carbonate and drying such slurries or wet masses to produce particulate products. The coprocessed products exhibit improved recompactibility, as compared to coprocessed products having lower microcrystalline cellulose:calcium carbonate weight ratios or as compared to physical dry blends of the two excipients.

7 Claims, No Drawings

MICROCRYSTALLINE CELLULOSE AND CALCIUM CARBONATE COMPOSITIONS USEFUL AS RECOMPACTIBLE PHARMACEUTICAL EXCIPIENTS

FIELD OF THE INVENTION

This invention relates to particulate compositions useful as excipients in pharmaceutical formulations and granulates and solid dosage forms containing such excipients and active pharmaceutical ingredients.

DESCRIPTION OF THE RELATED ART

Discrete dosages of pharmaceutical compositions suitable for oral administration are conveniently administered as solid dosage forms, typically tablets. In addition to the therapeutic ingredient or ingredients (commonly referred to as "actives," "active pharmaceutical ingredients," or "APIs"), the tablet comprises pharmaceutically acceptable materials, known as excipients, that are not actives and do not provide a therapeutic effect, but are added to the tablet formulation to confer specific properties not related to the activity of the active.

There are three general methods of preparation of tablets: (1) direct compression; (2) dry granulation; and (3) wet granulation. In direct compression, the powdered material(s) to be included in the tablet (including the active and the excipients) are blended together and compressed directly without intermediate processing, such as granulation. Although direct compression is the most effective and favorable manufacturing process for the production of solid dosage forms, such as tablets, many tablet formulations cannot be processed using direct compression due to certain properties of the formulations such as poor flow or low bulk density. For example, poor flow properties may result in unacceptably high variances in drug dosages from tablet to tablet.

Granulation procedures may be used where poor flow or low bulk density of the direct compression mix precludes tabletting by direct compression. Granulation also improves content uniformity of the active, and reduces dust generation. Dry granulation includes mixing the ingredients (which may include the active as well as one or more excipients such as binders, fillers, disintegrants, or lubricants), roller compacting or slugging the mix, dry screening or milling to a coarse dry granulate and compressing the granules. The granules may be combined with one or more further excipients (binder, disintegrant, lubricant, etc.) prior to recompaction. The wet granulation procedure includes mixing some or all of the ingredients and thereafter adding water to the mixed powders (alternatively, one or more of the ingredients, particularly a binder, may be in suspension or solution when combined with the other ingredients). The resulting wet mass is screened, dried, optionally combined with one or more further excipients such as a lubricant, binder, filler or disintegrant, and compressed into tablets.

In dry granulation, the tablet ingredients are not exposed to moisture, solvents and heat. Thus, dry granulation can be used to process moisture, solvent and/or heat sensitive actives. Dry granulation can be carried out by slugging or by roller compaction. Slugging is a double compression process. The material to be tabletted is compressed to a large compressed mass, or "slug," which is milled to a granulate, with the granulate then converted to tablets by a second compression process. Because slugging is a slow and uneconomic process, roller compaction has become the method of choice for dry granulation. Roller compaction has all the benefits of a granulation process, such as improved material flow behavior and content uniformity. In addition, roller compaction is high-volume and more economical to operate than wet granulation.

During the roller compaction process, at least a portion of the tablet formulation (the "granulate formulation") is compacted and densified by two counter-rotating high-pressure rollers, and the resulting material is milled to uniform size. The resulting granulate may be subsequently tabletted with or without additional excipients to form tablets. The tablet is formed by pressure acting on the tablet formulation in a die on a tablet press. A tablet press includes a lower punch which fits into a die from the bottom and an upper punch having a corresponding shape and dimension, which enters the die cavity from the top after the tablet formulation fills the die cavity. The tablet is formed by pressure applied to the tablet formulation in the die by the lower and upper punches.

Because of its inherent compactibility characteristics, microcrystalline cellulose (MCC) finds widespread use as an excipient in pharmaceutical formulations. Good binding and disintegration properties are also obtained when MCC is used in tablet formulations.

Tablet formation by roller compaction followed by tabletting includes two compaction steps. However, after the first compaction step, the MCC granulate may have insufficient compactibility for the second compaction, i.e., tabletting, step. Therefore a need exists for binders that can be used to prepare solid dosage forms by processes involving multiple compaction steps such as roller compaction and tabletting, or slugging. The binder must have sufficient compactibility for the second compaction step. Unfortunately, adequate recompactibility has proven to be challenging to achieve.

U.S. Pat. No. 4,744,987 discloses a particulate coprocessed microcrystalline cellulose and calcium carbonate composition having the respective components present in a weight ratio of from about 75:25 to 35:65. Such compositions are described as useful pharmaceutical excipients which may be employed in a direct compression tabletting process. However, the patent does not disclose using such a coprocessed composition in a recompaction process wherein a granulate is prepared from a compacted powder and then recompacted to provide a solid dosage form. Additionally, the preparation and use of coprocessed compositions having a microcrystalline cellulose:calcium carbonate weight ratio of greater than 75:25 is not described.

U.S. Pat. Pub. No. 2008-0213360 discloses an example wherein VITACEL® VE-650, a coprocessed microcrystalline cellulose:calcium carbonate product containing 65 parts by weight microcrystalline cellulose and 35 parts by weight calcium carbonate, was compacted to produce a compact, which was then milled to form a granulate. The granulate was subjected to a secondary compaction (i.e., a recompaction). The published application does not, however, disclose the use of coprocessed materials having higher microcrystalline cellulose:calcium carbonate weight ratios.

BRIEF SUMMARY OF THE INVENTION

The invention provides a coprocessed composition useful as a pharmaceutical excipient comprising particles of calcium carbonate and particles of microcrystalline cellulose (the composition hereinafter sometimes being referred to as "the particulate product of the invention"). A relatively high proportion of microcrystalline cellulose is used. For example, the weight ratio of microcrystalline cellulose:calcium carbonate can be at least 70:30 or at least 72.5:27.5 or at least 75:25 or greater than 75:25 (e.g., about 80:20). Increasing such weight ratio, at least up to a certain value, has unexpectedly been found to improve the recompactibility characteristics of granules prepared using such a coprocessed product as an excipient.

The term "coprocessed" as used in this specification refers to the physical processing of the calcium carbonate with microcrystalline cellulose in a manner that imparts improved physical characteristics to the coprocessed mixture, not exhibited by either microcrystalline cellulose or calcium carbonate alone or by simple blends or dry mixtures of microcrystalline cellulose and calcium carbonate. Such coprocessing may be accomplished, for example, by the mixing of the two components dispersed in an aqueous medium or by forming a wet mass of the two components, followed by drying to recover the coprocessed composition.

The microcrystalline cellulose and calcium carbonate are intimately associated in the particulate product of the invention and may be present as agglomerates of the two components. For example, at least a portion of the calcium carbonate particles may be embedded within the pores of the microcrystalline cellulose particles. The particulate product of the invention may be obtained by forming an aqueous slurry of the two components and then drying the slurry or by granulating the two components in the presence of water (i.e., a wet granulation) and drying.

As mentioned previously, coprocessed microcrystalline cellulose/calcium carbonate having relatively low microcrystalline cellulose/calcium carbonate weight ratios have previously been used in pharmaceutical formulations to be compacted into tablets and the like. However, it has now been unexpectedly discovered that a coprocessed product having a higher microcrystalline cellulose:calcium carbonate weight ratio exhibits improved recompactibility. That is, at a given compaction pressure, a tablet or other solid dosage form produced using a granulate (granules) prepared using the particulate product of the invention has a higher tensile strength than an analogous tablet produced using a granulate prepared from an excipient which contains a lower amount of microcrystalline cellulose relative to calcium carbonate. Alternatively, to achieve a desired tensile strength in a tablet or other solid dosage form, a lower compaction pressure is needed when the granulate uses the particulate product of the invention in place of a coprocessed product having a lower microcrystalline cellulose:calcium carbonate weight ratio. The need to use extragranular excipients is reduced or avoided altogether due to the improved recompaction characteristics of the particulate product furnished by the present invention. These results were surprising, in view of the fact that pure microcrystalline cellulose generally exhibits less than completely satisfactory recompactibility.

The present invention provides a composition comprising granules, wherein at least a portion of the granules are individually comprised of both a coprocessed composition comprising calcium carbonate and microcrystalline cellulose, wherein the weight ratio of microcrystalline cellulose:calcium carbonate is from 70:30 up to 85:15, and at least one additional component selected from the group consisting of actives, lubricants, disintegrants and binders. Thus, in one embodiment of the invention, granules are prepared by roller compacting a dry mixture comprising the particulate product of the invention and at least one active pharmaceutical ingredient (API), optionally also comprising at least one disintegrant and/or at least one lubricant and/or at least one filler, and grinding (milling) the resulting compacted ribbon to produce granules. The granules are then compacted to form tablets or other solid dosage forms. Alternatively, the granules may also be used as such (without being recompacted) in sachets or hard capsules, for example. In one embodiment, the granules have a median particle size of from about 50 to about 1500 microns, although the median particle size of the granules could be smaller or larger than these values.

In yet another aspect, a granulate or tablet formulation is provided which comprises at least one active (i.e., an API) and a particulate product obtained by a process comprising:
a) forming a well-dispersed aqueous slurry or wet mass of microcrystalline cellulose and calcium carbonate, wherein microcrystalline cellulose and calcium carbonate are present in a weight ratio of at least 70:30 or at least 72.5:27.5 or at least 75:25 or greater than 75:25 but not more than 85:15 (e.g., about 80:20); and
b) drying the aqueous slurry or wet mass by removing water therefrom to yield a particulate product.

Still another aspect of the invention provides a method for making granules, wherein the method comprises the steps of:
a) applying pressure to a granulate formulation to form a compact; and
b) milling the compact to form granules;
wherein the granules comprise at least one active (i.e., an API) and a particulate product obtained by a process comprising:
a) forming a well-dispersed aqueous slurry or wet mass of microcrystalline cellulose and calcium carbonate, wherein microcrystalline cellulose and calcium carbonate are present in a weight ratio of at least 70:30 or at least 72.5:27.5 or at least 75:25 or greater than 75:25 but not more than 85:15 (e.g., about 80:20); and
b) drying the aqueous slurry or wet mass by removing water therefrom to yield a particulate product.

The granules thus obtained may be recompacted to provide a solid dosage form such as a tablet.

Further provided by the invention is a solid dosage form comprising a particulate product, at least one active, and, optionally, at least one additional excipient (e.g., a filler, binder, lubricant, disintegrant, and/or glidant) in the form of a compacted tablet, wherein the particulate product is obtained by a process comprising:
a) forming a well-dispersed aqueous slurry or wet mass of particulate microcrystalline cellulose and at least one calcium carbonate, wherein microcrystalline cellulose and calcium carbonate are present in a weight ratio of at least 70:30 or at least 72.5:27.5 or at least 75:25 or greater than 75:25 but not more than 85:15 (e.g., about 80:20); and
b) drying the aqueous slurry or wet mass by removing water therefrom.

DETAILED DESCRIPTION OF CERTAIN EMBODIMENTS OF THE INVENTION

In one embodiment, the particle size of the coprocessed particulate product of the present invention is such that substantially all of the particles have a particle size less than a No. 60 sieve (250 μm) and preferably have a median particle size in the range of from 20 μm to 150 μm.

The particulate product may advantageously be prepared by forming a well-dispersed aqueous slurry or wet mass of microcrystalline cellulose and calcium carbonate, both being present in particulate form. The amounts of each component are, in one aspect of the invention, selected to provide a component ratio in the range of from 85:15 to 70:30 (on a weight basis) or in the range of from 85:15 to 75:25 (on a weight basis) or about 80:20 (on a weight basis) microcrystalline cellulose:calcium carbonate for the particulate product. The aqueous slurry or wet mass is dried by removing water therefrom, to yield the particulate product of the invention.

The aqueous well-dispersed slurry of the two components is preferably formed by introducing microcrystalline cellulose and calcium carbonate into an aqueous medium in amounts that yield a relatively concentrated slurry of at least 10 wt % but no more than 40 wt % solids. The order of addition of the components is not believed to be particularly critical. Preferably, the slurry remains liquid (non-pasty), free-flowing, and relatively low in viscosity. In various embodiments of the invention, the viscosity of the slurry is not greater than about 40,000 cps, not greater than about 10,000 cps, or not greater than about 5000 cps. The aqueous slurry is preferably dried by spray drying to yield the particulate product.

In another embodiment of the invention, the particulate product may be obtained by preparing a wet mass containing microcrystalline cellulose and calcium carbonate, followed by drying. For example, the microcrystalline cellulose and calcium carbonate may be combined together with a relatively small amount of water, e.g., an amount sufficient to provide a wet paste. Mixing of the two components is advantageously carried out under conditions effective to achieve intimate association of the particles of each component. For example, the wet mass may be subjected to high shear mixing. In one embodiment, dry microcrystalline cellulose, dry calcium carbonate and water are separately added to form the wet mass. However, in other embodiments, one or both of the microcrystalline cellulose and/or calcium carbonate is/are already wet when combined (for example, microcrystalline cellulose wet cake, i.e., "never dried" microcrystalline cellulose, may be utilized).

The particulate product of this invention contains two essential components, microcrystalline cellulose and calcium carbonate.

In one aspect of the invention, microcrystalline cellulose and calcium carbonate are the only constituents of the particulate product. However, one or more other ingredients may also be incorporated into the particulate product during its preparation. These are ordinarily present in relatively small amounts, representing less than 30%, and preferably less than 20%, of the total particulate product weight. Such additives may be incorporated to facilitate the coprocessing procedure, particularly during the drying step, or to provide enhanced properties for the particulate product in its use as a pharmaceutical excipient. Examples of additives in these categories are binders, e.g., water-soluble gums like hydroxypropylmethylcellulose, methylcellulose, polyvinylpyrrolidone, etc.; lubricants, e.g., long chain fatty acid esters or salts thereof like palmitic and stearic acids and alkali metal and alkaline earth metal salts thereof; and disintegrants like cross-linked carboxymethylcellulose, starch, etc.

The particulate product of this invention possesses desirable performance attributes that are not shown with the corresponding dry-blend of microcrystalline cellulose particles and calcium carbonate particles. The mechanism that occurs during the coprocessing procedure in accordance with this invention is not fully understood but appears to yield a particulate product in which the two essential components are in intimate association with each other. This intimate association or admixture of microcrystalline cellulose and calcium carbonate cannot be achieved through simple dry blending of these materials.

This intimate association of the two components manifests itself in the appearance of agglomerated particles, containing both microcrystalline cellulose and calcium carbonate, that result after drying of the slurry. Without being bound to a particular theory, it is believed that at least a portion of the calcium carbonate particles may be embedded within the pores of the microcrystalline cellulose particles. Generally speaking, it will be desirable for the median particle size of the microcrystalline cellulose to be greater than the median particle size of the calcium carbonate. For example, in certain embodiments the median particle size of the microcrystalline cellulose will be at least two, three, four or five times greater than the median particle size of the calcium carbonate.

Various characteristics of the particulate product, e.g., its particle size, moisture content, bulk density, will be described in detail below, in the context of the process by which this particulate product may be prepared. These physical characteristics are in large measure dependent on the manner in which the microcrystalline cellulose and calcium carbonate are coprocessed. For example, the drying conditions may affect such characteristics.

An exemplary process for preparing the particulate product of this invention involves forming a well-dispersed aqueous slurry or wet mass of microcrystalline cellulose and calcium carbonate, in which both materials are present as particulate solids. The relative amounts of the two components are adjusted in the slurry or wet mass to yield the specific weight ratio desired in the recovered coprocessed product. Since the weight ratio of the two components in the particulate product corresponds closely to that in the precursor well-dispersed slurry or wet mass, this ratio adjustment is relatively straightforward and would be readily ascertainable by one of ordinary skill in the art.

The process next involves drying the aqueous slurry by removing water from it to yield the particulate product. As mentioned earlier, spray drying is the preferred drying means but other drying methods, e.g., flash drying, fluidized bed drying, ring drying, micron drying, tray drying, vacuum drying, oven drying, radio frequency drying and microwave drying, may also be adapted for use in this coprocessing step.

The two components employed in forming the well-dispersed aqueous slurry or wet mass are microcrystalline cellulose and calcium carbonate, although one or more additional components may also be utilized if so desired. The source and nature of these components are not considered critical. In one embodiment, the microcrystalline cellulose is wet cake from a conventional microcrystalline cellulose manufacturing process. The wet cake is material which has not yet been dried, sometimes termed "never dried" or hydrocellulose. The microcrystalline cellulose source may also be a conventional product which has already been dried.

The particle size of the microcrystalline cellulose used in the aqueous slurry or wet mass is ordinarily that which is encountered in conventional microcrystalline cellulose product, or in its precursor wet cake, i.e., never dried product. The particle size is desirably such that substantially all particles are less than No. 60 sieve (250 μm) in size. In one embodiment, the microcrystalline cellulose has a median particle size of from about 20 μm to about 250 μm.

Specific size requirements for fine particle sizes, if desired, can be met through screening off unwanted coarse material or through conventional wet or dry attrition procedures. Such attrition may also be accomplished with the microcrystalline cellulose in the aqueous slurry or wet mass. These size reduction procedures are ordinarily not required with microcrystalline cellulose as is now commercially produced.

The calcium carbonate employed in the present invention may be any of the various grades or types of calcium carbonate known in the art, particularly the pharmaceutical excipient art. For example, the calcium carbonate may be precipitated calcium carbonate or ground limestone. The use of USP or Ph. Eur. grades of calcium carbonates is also preferred. For example, the calcium carbonates sold under the brand name ViCALity® Albaglos, USP/FCC precipitated calcium carbonate, supplied by Specialty Minerals, are suitable for use in the present invention.

Calcium carbonate sizing is preferably such that substantially all particles are less than 200 μm in size and, more preferably, less than 50 μm. The median particle size of the calcium carbonate is desirably less than 100 μm and, more preferably, is less than 50 μm or less than 20 μm. In one embodiment, the median particle size of the calcium carbonate is about 0.1 to about 10 μm, e.g., about 1 μm.

Both microcrystalline cellulose and calcium carbonate, it should be recognized, are substantially insoluble in water. Consequently, the particle size of the material present in the well-dispersed aqueous slurry or wet mass is directly related to the sizing of the two components introduced to the slurry or wet mass; i.e., there is no appreciable dissolution of either of the two components in the aqueous slurry or wet mass (although some attrition of the microcrystalline cellulose particles may take place).

The aqueous slurry of these two components may be prepared in any of several ways. The two solid components may both be introduced into a single aqueous medium, or each may be introduced separately into separate aqueous media which are then combined, or other analogous procedures may be devised.

One procedure involves dispersing the microcrystalline cellulose alone into an aqueous solution, preferably water. Typical solids concentrations for this aqueous mixture are from 5-25 wt % microcrystalline cellulose but 10-20 wt % microcrystalline cellulose is preferred.

Once the microcrystalline cellulose is well-dispersed in the aqueous slurry, the appropriate amount of calcium carbonate can then be added, in dry form, with mixing being continued during its addition. The exact amount of calcium carbonate to be added depends on the microcrystalline cellulose content of the slurry and the ratio of the two components desired in the coprocessed product. Water may also be added if a more dilute slurry is desired, but this is usually not required. If so desired, the pH of the slurry may be adjusted by the addition of one or more pH adjusting agents, such as an acid or a base. Typically, the aqueous slurry has a pH within the range of about 8 to about 11.

The aqueous slurry or wet mass containing the two components should be well mixed to assure uniform dispersion of the components throughout the aqueous medium or wet mass. This is necessary to provide for a uniform, consistent component ratio in the particulate product, prepared via drying the aqueous slurry or wet mass.

The total solids content of the aqueous slurry is preferably at least 10 wt %, based on the total slurry weight, and is more preferably at least 20 wt % solids. The higher solids content levels are desirable since the amount of water that must be removed during the drying step is accordingly reduced. However, in one embodiment of the invention, the solids content is kept below the level at which the slurry no longer is liquid and capable of being readily stirred.

The upper limit on solids content in the aqueous slurry is also typically determined by the operating constraints of the drying apparatus used. With the preferred spray drying procedure, solids contents of 20-30 wt % are representative for aqueous slurries that can be readily processed.

The temperature of the aqueous slurry is not critical. Ambient temperatures, of from about 10 to about 25° C., are preferred. Higher slurry temperatures may be employed, and these may be desirable with certain types of drying equipment.

The drying of the well-dispersed aqueous slurry is preferably accomplished by spray drying of the slurry. Conventional spray drying equipment may be employed, and operating procedures that are familiar to those experienced in the spray drying art are applicable to the spray drying step of this process. Drier (drier gas) outlet temperature is ordinarily used to control the residual moisture level obtained in the coprocessed particulate product.

Moisture levels of not more than about 5 wt % $H_2O$ are generally desired in the particulate, dried product, although, of course, the water content may be higher than 5 wt % and may be readily controlled by varying the drying conditions.

In a spray-drying process, the aqueous slurry of microcrystalline cellulose and calcium carbonate may be atomized into droplets and brought together with a sufficient volume of hot air to produce evaporation and drying of the droplets. The dispersed slurry of microcrystalline cellulose and calcium carbonate preferably is pumpable and capable of being atomized. It is sprayed into a current of warm filtered air, which supplies the heat for evaporation and conveys a dried product to a collecting device. The air is then exhausted with the removed moisture. The coprocessed product comprises microcrystalline cellulose and calcium carbonate particles in intimate association with each other (typically, in the form of agglomerates).

In a spray drying procedure, drier outlet temperatures are ordinarily in the range of about 40 to about 100° C. Corresponding drier inlet temperatures are higher, ordinarily in the range of about 90 to about 300° C.

The coprocessed product recovered from the drying operation is a free-flowing particulate solid, that is typically a granular white powder in appearance. The particle size of the product is a function of the particle sizing of the microcrystalline cellulose and calcium carbonate in the aqueous slurry or wet mass and of the drying conditions employed for removing water from the slurry or wet mass. In the embodiment where an aqueous slurry is being dried, particle size may be influenced by spray dryer operating conditions, for example, such as droplet size, temperature, production rate, % slurry solids, type of atomizer, atomizer speed, air flow and chamber size. Furthermore, it is within the scope of the invention to sort or mechanically alter the dried coprocessed product so as to vary or select the particle size and particle size distribution as may be desired.

The particulate product in one embodiment of the invention has a particle size such that substantially all of the particles have a size smaller than a No. 60 sieve (250 μm). Median particle size of the particulate material is, in one embodiment, in the range of from about 20 μm to about 200 μm, and in another embodiment is in the range of from about 30 μm to about 50 μm. "Median particle size," as used herein, refers to the D50 value as measured by laser diffraction using a Malvern Mastersizer 2000. The loose bulk density of the particulate product is typically less than 0.60 g/cc and greater than 0.20 g/cc. The pH of the particulate product is generally about 8 to about 11.

The particulate product of the present invention is particularly useful as an excipient or binder in processes involving roller compaction, granulation, and/or tabletting.

For example, the particulate product may be utilized in the following process:
1) The particulate product is blended with an API, a filler, and a disintegrant;
2) The blend from step 1 is further blended with a lubricant, if needed to reduce sticking on the compaction rolls;
3) The blend is compacted, using a roller compactor;

4) The ribbon obtained by roller compaction is granulated and/or milled;
5) The granulate (granules) obtained from step 4 is screened (to control and/or modify the particle size of the granulate, as needed or desired);
6) The screened granulate is recompacted to form tablets.

If needed to improve stability or to modify the disintegration time and dissolution rate or profile of the tablets, extragranular disintegrant and/or lubricant may be blended with the screened granulate prior to step 6. However, in at least some embodiments of the invention, the productivity (operating cost) of the dry granulation process is improved by avoiding such additional steps, which are generally considered necessary in traditional roller compaction processes which utilize binders and fillers other than the particulate product described herein.

Roller compaction (also known in the art as "roll compaction") is a dry compaction/granulation process for tablet formation, which is used when a tablet formulation does not have the flow characteristics or high enough bulk density necessary for other methods of tablet formation. A roller compactor uses pressure to compact and densify the tablet formulation and to bind powders into granules. Actives that have been processed by roller compaction include, for example, acetylsalicylic acid (aspirin), acetaminophen, amoxicillin, ibuprofen, penicillin, ranitidine, and streptomycin.

The coprocessed particulate product of the present invention is especially suitable for use in connection with a granulation process. Granulation is a process of size enlargement in which small particles are gathered together into larger aggregates in which the original particles can still be identified. Uniformly mixed powders (granulate formulations) are compressed between counter rotating rollers to form a ribbon of compacted material that is then milled into granules. Thus, the coprocessed particulate product may be used as an ingredient in a granulate formulation which is then converted into a granulate (granules). A schematic representation of a roller compactor is shown in FIG. 3 of U.S. Patent Publication No. 2008/0213360, incorporated herein by reference in its entirety for all purposes. A roller compactor comprises a roller assembly, press frame, hydraulic pressure system, and a feed system. The feed system is located immediately before the rollers and determines the rate of flow of the granulate formulation to the rollers. The feed system may comprise one or more feed screws that force the granulate formulation between the compacting rollers. The granulate formulation is compacted as it passes through the two compacting rollers. The volume of the granulate formulation decreases as it passes through the region of maximum pressure, where it is formed into a solid compacted material known as a sheet or ribbon. Compaction pressure is provided by the hydraulic pressure system, which can be adjusted to produce the desired compaction pressure. The hydraulic pressure system acts on one of the rollers. As shown in FIG. 3 of U.S. Patent Publication No. 2008/0213360, the roller compaction process may be a continuous process of compacting, milling, screening, and recycling the too-large granules ("Overs") and too small granules ("Fines") back to the process. One advantage of the present invention is the reduction in the amount of Fines produced during such a process when the particulate product of the invention is employed as an excipient.

Various configurations for the rollers are well known in the art and are described, for example, in A. M. Falzone, Ph.D. Thesis, Purdue University, 1990 (U.M.I., Ann Arbor, Mich., Order Number 9313940). Roller compaction equipment is commercially available from the Fitzpatrick Company, Elmhurst Ill. USA as CHILSONATOR® roll compactors. This equipment is described in "Introduction to Roll Compaction and the Fitzpatrick CHILSONATOR," published by The Fitzpatrick Company Europe.

The particulate product of the present invention is also suitable for use as a component of a tablet, which may for example be prepared directly from a physical dry blend of the particulate product in combination with one or more additional ingredients such as an API or from a granulate prepared as previously described herein (also possibly in combination with one or more additional ingredients). Tabletting is well known to those skilled in the art of tablet formation. The tablet is formed by pressure being applied to the tablet formulation on a tablet press. A tablet press includes a lower punch, which fits into a die from the bottom, and an upper punch having a corresponding shape and dimension, which enters the die cavity from the top after the tablet formulation fills the die cavity. The tablet is formed by pressure applied to the tablet formulation in the die by the lower and upper punches. The ability of the tablet formulation to flow freely into the die is important in order to ensure that there is a uniform filling of the die with continuous flow of tablet formulation from hopper to die. A lubricant, such as magnesium stearate, may be added to facilitate ejection of the tablet from the die following compaction, and to avoid sticking to the punch faces. Tabletting is well described in pharmaceutics textbooks such as AGENNARO, Remington: The Science and Practice of Pharmacy, 20th Ed., Lippincott Williams & Wilkins, Baltimore, Md., 2000.

In one aspect, the present invention provides a solid dosage form such as a tablet comprising the particulate product of the invention, one or more actives, and, optionally, one or more pharmaceutically acceptable excipients. Such tablets may be prepared from a tablet formulation by combining the active or actives with at least one excipient according to conventional pharmaceutical compounding techniques. To prepare a solid dosage form, or tablet, by direct compaction, the tablet formulation must have the necessary physical characteristics. Among other things, the tablet formulation must be free flowing, must be lubricated, and, importantly, must possess sufficient compactibility to ensure that the solid dosage form remains intact after compaction, and is robust enough for subsequent operations, such as handling, coating, and packaging. The particulate product of the present invention has been found to impart unexpectedly improved properties to tablet formulations, particularly with respect to compactibility and recompactibility.

The tablet may be formed by pressure being applied to the tablet formulation on a tablet press. A tablet press includes a lower punch that fits into a die from the bottom and an upper punch having a corresponding shape and dimension that enters the die cavity from the top after the tablet formulation fills the die cavity. The tablet is formed by pressure applied on the lower and upper punches. The ability of the tablet formulation to flow freely into the die is important in order to ensure that there is a uniform filling of the die and a continuous movement of the material from the source of the tablet formulation, e.g., a feeder hopper. The lubricity of the tablet formulation is crucial in the preparation of the solid dosage forms because the compressed material must be readily released from the punch faces. The tablet must also eject cleanly from the die following compression.

Because actives do not always have these properties, methods of tablet formulation have been developed in order to impart these desirable characteristics to the tablet formulation. Typically, the tablet formulation comprises one or more additives, or excipients, that impart the desired free flowing, lubrication, and binding properties to the tablet formulation.

The excipients for dry granulate formulations should have good recompactibility and dilution potential to allow compaction of the granules into a tablet. The excipients should not accelerate chemical and/or physical degradation of the active and should not interfere with its biological availability. The excipients should be physiologically inert and should not adversely interfere with the desired tablet disintegration or dissolution of the active. They should show low lubricant sensitivity and ensure acceptable active content uniformity. Typical excipients are selected from the group consisting of binders, disintegrants, glidants, fillers, diluents, colorants, flavorants, stabilizers, and lubricants. The choice of the excipients and the composition of the tablet formulation depend on the active, the amount of active in the formulation, the type of tablet, the desired characteristics for both the tablet formulation and the resulting tablet, and the manufacturing process used. These include prompt release, for which the drug dissolves in a very short time, immediate release and modified release, which include most of the orally administered tablets that are swallowed.

Pharmaceutically acceptable excipients are well known to those skilled in the art and are disclosed for example, in Staniforth, U.S. Pat. No. 6,936,277, and Lee, U.S. Pat. No. 6,936,628, each of which is incorporated herein by reference in its entirety for all purposes. Excipients such as diluents, binders, glidants, and lubricants are added as processing aids to make the tabletting operation more effective. Still other types of excipients enhance or retard the rate of disintegration of the tablet, improve the taste of the tablet, (for example, sweetening agents), or impart a color or flavor to the tablets.

One or more lubricants may be added to a tablet formulation comprising the particulate product of the present invention to prevent the formulation from sticking to the punches during tablet manufacture. Suitable lubricants include, for example, fatty acids, fatty acid salts, and fatty acid esters such as magnesium stearate, calcium stearate, stearic acid, sodium stearyl fumarate, hydrogenated vegetable oil and the like. Lubricants may typically comprise about 0.1 wt % to about 3.0 wt % or about 0.5 wt % to about 1 wt % of the formulation.

Antiadherents may be utilized to prevent sticking of the tablet formulation to the punch face and die wall. They are used in combination with magnesium stearate when sticking is a problem. Commonly used antiadherents are cornstarch and talc.

Diluents, fillers, or bulking agents in addition to the particulate product of the present invention may be added in order to increase the bulk weight of the material to be tabletted in order to make the tablet a practical size. This is often necessary where the dose of the active is relatively small. Suitable fillers for this purpose include, but are not limited to, lactose, dibasic calcium phosphate and other calcium phosphates, powdered cellulose, dextrates, isomalt, calcium carbonate, magnesium carbonate, starch, pre-gelatinized starch, microcrystalline cellulose and mixtures thereof. Sugar alcohols such as sorbitol, mannitol and xylitol may also be used as fillers, especially in chewable tablet formulations. The most significant differences between sorbitol and mannitol are hygroscopicity and solubility. Sorbitol is hygroscopic above 65% relative humidity and mannitol is nonhygroscopic. The aqueous solubility of sorbitol is higher than mannitol.

One or more binders in addition to the particulate product of the present invention may be added to further modify the cohesive qualities of the powdered material(s). Suitable additional binders include starch, microcrystalline cellulose, and sugars such as sucrose, glucose, dextrose, and lactose. One or more stabilizers may be included in the tablet formulation to reduce the rate at which the active decomposes. Suitable stabilizers include antioxidants, such as ascorbic acid. Additionally, one or more disintegrants may also be included in the tablet formulation to ensure that the tablet has an acceptable dissolution rate in an environment of use (such as the gastrointestinal tract). The disintegrant breaks up the tablets and the granules into particles of active and excipients. Superdisintegrants such as croscarmellose sodium, sodium starch glycolate, or crospovidone may also be employed.

One or more glidants may be used in the tablet formulation to improve flow. Because of the shape and size of the particles, glidants improve flow in low concentrations. They may be mixed in the final tablet formulation in dry form. Suitable glidants include, for example, alkali metal stearates, colloidal silicon dioxide (including materials sold under the brand names CAB-O-SIL®, SYLOID®, and AEROSIL®), and talc.

Desirable characteristics may be imparted to the tablet by colorants (i.e., dyes and pigments), natural or artificial sweeteners, and flavorants. Wetting agents, also called surface active agents or surfactants, may also be present. The tablet may also be coated.

Surfactants such as polysorbates, sodium lauryl sulphate, polyethylene glycol fatty acid esters, or polyethylene glycol ester salts may also be present in the formulation. To modify the release profile of the API, one or more matrix formers such as HPMC, carrageenan or alginate may optionally be included.

Tablets in accordance with the present invention may be any desired shape and size. For example, the size of round tablets may be about 50 mg to 500 mg and capsule-shaped tablets may be about 200 mg to 1200 mg in size. However, other formulations prepared in accordance with the invention may be suitably sized and shaped for other uses or locations, such as other body cavities, e.g., periodontal pockets, surgical wounds, and vaginally. For certain uses, such as chewable tablets, antacid tablets, vaginal tablets, and implants, the tablet may be larger.

The compositions are also suitable for use in enrobing processes to prepare solid dose forms. For example, solid dose forms may be prepared by lightly compacting a tablet formulation or granulate formulation in accordance with the present invention to form a powder compact and enrobing the powder compact with a film. The methods and apparatus for forming enrobed solid dose forms disclosed in WO 03/096963, WO 2005/030115, WO 2005/030116, WO 2005/030379, and WO 2006/032828, the disclosures of which are all incorporated herein by reference in their entirety for all purposes, may, for example, be adapted for use with solid dose forms prepared using the particulate products of the present invention.

The MCC/calcium carbonate-containing materials of the invention may be used as binders in solid dosage forms, such as tablets, that comprise one or more actives, and optionally, one or more other excipients. They are particularly useful as binders for formulations prepared by direct compression or processes involving compaction, granulation and recompaction. Although primarily useful in pharmaceutical and veterinary applications, they may be used in other areas, such as agriculture, food, cosmetics, and other industrial applications.

EXAMPLES

Glossary

| | |
|---|---|
| AVICEL ® PH-101 | 50 µm microcrystalline cellulose (FMC, Philadelphia PA) |
| AVICEL ® PH-102 | 100 µm microcrystalline cellulose (FMC, Philadelphia PA) |

| | -continued | |
|---|---|---|
| calcium carbonate | ViCALity ® Albaglos, precipitated calcium carbonate (Specialty Minerals Inc., Minerals Technologies Inc., New York, NY) | |
| magnesium stearate | Vegetable 2257 (Tyco Mallinckrodt, St Louis, MO) | |
| Vitamin C | ascorbic acid (crystalline) (Jiangsu Jiangshan Pharmaceutical Co., Ltd) | |

Unless otherwise stated, all percentages or proportions provided herein are stated as percentages or proportions based on weight.

Preparation and Methods

Roller-compacted ribbons and granulates were prepared and tested as follows: Formulations containing 30 wt % Vitamin C were prepared by making a preblend of 6.95 kg of binder excipient(s) with 3 kg of Vitamin C as a model drug and blending for 10 minutes in a Pharmatech 50 Litre V Container rotating at 28 rotations per minute. Then 50 grams of magnesium stearate was added as a lubricant to the preblend and mixed for 2 minutes at 28 rpm. The blend, a total of 10 kg, was discharged. The same steps were repeated to produce a second blend of 10 kg using the same ingredients. The second blend was then discharged into the same bag as the first blend to obtain 20 kilograms. The formulation may be used for direct compression (e.g., to prepare tablets) or for forming granules (which may be recompacted to form tablets or other solid dosage forms).

The formulations were roller-compacted and then milled to form granulates at Fitzpatrick (The Fitzpatrick Company Europe, Entrepotstraat 8, B-9100 Sint-Niklaas, Belgium) on a pilot scale Chilsonator model IR-520/D6A. The roller compactor was equipped with knurled (grooved) rolls. The feeding auger or horizontal screw was rotating at 12 rpm, and the tamping auger or vertical screw was rotating at 200 rpm. These screw speeds were kept constant throughout the experiments. Compaction pressures were set at 20, 30 or 40 bars to compact the granulate formulations into a ribbon. The resulting gap or distance between the compaction rolls ranged between 1.2 and 1.8 millimeters depending on the compaction pressure applied on the powder/compact and on the granulate formulation being compacted. The mill used was of the type bar rotor rotating at 500 rpm and used in combination with a rasping screen having 1.0 millimeter openings. Approximately 2 kg of granulate were collected at each compaction pressure for each granulate formulation evaluated. Granulate from ribbons compacted at 30 bars was then compressed to form tablets on an ESH Compaction Simulator equipped with 13 millimeter round and flat punches. Compression force was applied only by the upper punch, while the lower punch was fixed during compression. The speed of the compaction simulator was set to obtain a mean compression (vertical) speed for the upper punch of 300 millimeters per second, which corresponds to a dwell time of approximately 6 milliseconds. Dwell time was defined as the time during which more than 90% of the maximum force is applied.

Example 1

A series of coprocessed microcrystalline cellulose/calcium carbonate compositions was prepared by mixing aqueous slurries of microcrystalline cellulose (wet cake) and calcium carbonate in weight ratios ranging from 90:10 to 50:50 microcrystalline cellulose:calcium carbonate and spray drying the slurries. Certain characteristics of the compositions thereby obtained are shown in Table 1.

TABLE 1

| Example | MCC:Ca Carbonate Weight Ratio | Loss on Drying, % | Sieve Fraction + 200 mesh, % | Loose Bulk Density, g/cc |
|---|---|---|---|---|
| 1-1 | 90:10 | 3.4 | 24 | 0.41 |
| 1-2 | 80:20 | 3.4 | 22 | 0.42 |
| 1-3 | 75:25 | 3.3 | 23 | 0.41 |
| 1-4 | 65:35 | 2.7 | 25 | 0.45 |
| 1-5 | 50:50 | 2.1 | 26 | 0.50 |

The effect of the weight ratio of microcrystalline cellulose to calcium carbonate in the coprocessed composition on recompactibility was evaluated by tabletting roller-compacted Vitamin C-containing granules. The 30% Vitamin C granulate formulations containing the different excipients were compacted in a first compaction step (a ribbon was produced by roller compaction at 30 bars), ground to produce granules, and then the granules were compacted in a second compaction step (tabletting) at a tabletting pressure of 120 MPa. The results are shown in Table 2. Granules containing coprocessed MCC:calcium carbonate particulate products having weight ratios of 80:20 and 75:25 outperformed granules containing particulate products prepared using higher (90:10) or lower (65:35 and 50:50) weight ratios. That is, the tablet tensile strength was enhanced when the weight ratio of microcrystalline cellulose:calcium carbonate was 75:25 to 80:20, with tensile strength decreasing at higher or lower weight ratios.

TABLE 2

| Example | MCC:Ca Carbonate Weight Ratio | Tensile Strength, MPa 120 MPa Tabletting Pressure |
|---|---|---|
| 1-1 | 90:10 | 1.06 |
| 1-2 | 80:20 | 1.27 |
| 1-3 | 75:25 | 1.28 |
| 1-4 | 65:35 | 1.16 |
| 1-5 | 50:50 | 0.98 |

Example 2

Example 1 was repeated, but the coprocessed microcrystalline cellulose/calcium carbonate composition was prepared using AVICEL® PH-101 microcrystalline cellulose instead of microcrystalline cellulose wet cake and an MCC:calcium carbonate weight ratio of 77.5:22.5. Good recompactibility performance was observed when this composition was used to prepare roller-compacted granules. When the granules were recompacted into tablets at a pressure of 120 MPa, the tensile strength of the tablets was 1.25 MPa. When AVICEL® PH-102 was substituted for AVICEL® PH-101 in preparing the coprocessed composition, the tablets produced using recompacted granules prepared from the coprocessed composition had a tensile strength of 1.33 MPa. By way of comparison, granules prepared using VITACEL® VE-650 (a coprocessed composition having an MCC:calcium carbonate weight ratio of 65:35) yielded tablets having a tensile strength of 1.09 MPa when recompacted at 120 MPa. Additionally, granules prepared using a physical dry blend of AVICEL® PH-102 and calcium carbonate in a 77.5:22.5 weight ratio exhibited a tablet tensile strength of only 0.33 MPa when recompacted at a tabletting pressure of 120 MPa. This example demonstrates the significant loss of recompactibility performance that results if the MCC:calcium carbonate is not coprocessed in accordance with the present invention.

What is claimed is:

1. A composition comprising granules, wherein the granules comprise (i) a coprocessed composition consisting of a calcium carbonate and microcrystalline cellulose, wherein the weight ratio of microcrystalline cellulose:calcium carbonate is from 70:30 to 85:15, and (ii) at least one component selected from the group consisting of actives, lubricants, disintegrants, glidants, diluents, colorants, flavorants, stabilizers, fillers and binders; wherein a tablet made from the composition has a higher tensile strength at a tabletting pressure of 120 MPa than the same tablet having a weight ratio of microcrystalline cellulose to calcium carbonate less than 70:30.

2. The composition of claim 1, wherein the granules have a median particle size of from about 50 to about 1500 microns.

3. The composition of claim 1, wherein the weight ratio of microcrystalline cellulose:calcium carbonate is from about 75:25 to about 85:15.

4. The composition of claim 1, wherein the weight ratio of microcrystalline cellulose:calcium carbonate is about 80:20.

5. A method comprising the steps of:
a) applying pressure to a granulate formulation to form a compact, wherein the granulate formulation comprises a coprocessed composition consisting of calcium carbonate and microcrystalline cellulose, wherein the weight ratio of microcrystalline cellulose:calcium carbonate is from 70:30 to 85:15, and at least one additional component selected from the group consisting of actives, lubricants, disintegrants, glidants, diluents, colorants, flavorants, stabilizers, fillers and binders; and
b) milling the compact to form granules;
wherein a tablet made from the granules has a higher tensile strength at a tabletting pressure of 120 MPa than the same tablet having a weight ratio of microcrystalline cellulose to calcium carbonate less than 70:30.

6. The method of claim 5, wherein the milling is carried out under conditions effective to provide granules having a median particle size of from about 50 to about 1500 microns.

7. A method of producing a solid dosage form, said method comprising compacting the composition as claimed in claim 1.

* * * * *